US011596326B2

(12) United States Patent
Vicario et al.

(10) Patent No.: US 11,596,326 B2
(45) Date of Patent: Mar. 7, 2023

(54) SYSTEMS AND METHODS FOR METABOLIC MONITORING

(71) Applicant: KONINKLIJKE PHILIPS N.V., Eindhoven (NL)

(72) Inventors: Francesco Vicario, Boston, MA (US); Eric Paul Wigforss, Wallingford, CT (US)

(73) Assignee: Koninklijke Philips N.V., Eindhoven (NL)

( * ) Notice: Subject to any disclaimer, the term of this patent is extended or adjusted under 35 U.S.C. 154(b) by 405 days.

(21) Appl. No.: 17/023,424

(22) Filed: Sep. 17, 2020

(65) Prior Publication Data

US 2021/0169370 A1    Jun. 10, 2021

Related U.S. Application Data

(60) Provisional application No. 62/944,388, filed on Dec. 6, 2019.

(51) Int. Cl.
*A61B 5/097* (2006.01)
*A61B 5/083* (2006.01)
*A61B 5/00* (2006.01)

(52) U.S. Cl.
CPC ............ *A61B 5/097* (2013.01); *A61B 5/0833* (2013.01); *A61B 5/0836* (2013.01); *A61B 5/6819* (2013.01); *A61B 2562/0247* (2013.01)

(58) Field of Classification Search
CPC ..... A61B 5/097; A61B 5/0833; A61B 5/0836; A61B 5/6819; A61B 2562/0247; A61B 2505/07
See application file for complete search history.

(56) References Cited

U.S. PATENT DOCUMENTS

| 7,640,932 B2 | 1/2010 | Chua et al. |
| 2010/0113956 A1 * | 5/2010 | Curti .................. A61M 16/085 600/538 |

(Continued)

FOREIGN PATENT DOCUMENTS

| GB | 2509922 A | 7/2014 |
| GB | 2523180 A | 8/2015 |

(Continued)

*Primary Examiner* — Andrey Shostak
(74) *Attorney, Agent, or Firm* — Daniel H. Brean

(57) ABSTRACT

The present disclosure describes a system for metabolic monitoring comprising: collecting exhaled gas from nasal airways of a subject; a mixing chamber for receiving a portion of the exhaled gas; a plurality of sensors for outputting signals related to gas parameters related to inhaled gas and exhaled gas during one or more breaths; and processors configured to determine a flow rate of gas in the interface appliance; determine pressure changes near the mouth of the subject to detect mouth breathing of the subject; determine concentration measurements of O2 and CO2 of the portion of the exhaled gas in the mixing chamber, and discard concentration measurements corresponding to mouth breathing; determine a rate of oxygen consumption VO2 and a carbon dioxide production VCO2 of the subject based on the determined flow rate, the CO2 concentration, and the determined O2 concentration.

21 Claims, 5 Drawing Sheets

(56) References Cited

U.S. PATENT DOCUMENTS

| | | | |
|---|---|---|---|
| 2015/0059759 A1* | 3/2015 | Frater | A61M 16/0622 128/205.25 |
| 2015/0119743 A1* | 4/2015 | Maksym | A61B 5/087 600/533 |
| 2015/0265184 A1* | 9/2015 | Wondka | A61B 5/082 600/532 |
| 2016/0150995 A1* | 6/2016 | Ratto | A61B 5/4875 600/532 |
| 2018/0125391 A1 | 5/2018 | Candell | |

FOREIGN PATENT DOCUMENTS

| | | | |
|---|---|---|---|
| WO | 2005051188 A1 | 6/2005 | |
| WO | 2019094680 A1 | 5/2019 | |

* cited by examiner

SYSTEMS AND METHODS FOR METABOLIC MONITORING

CROSS-REFERENCE TO RELATED APPLICATIONS

This patent application claims the priority benefit under 35 U.S.C. § 119(e) of U.S. Provisional Application No. 62/944,388, filed on Dec. 6, 2019, the contents of which are herein incorporated by reference.

BACKGROUND

1. Field

The present disclosure pertains to systems and methods for metabolic monitoring.

2. Description of the Related Art

The present disclosure relates to systems and methods for metabolic monitoring. Existing commercial devices cover several applications, including mechanically ventilated critical patients, specialized visits (e.g., with a dietician or nutritionist), spot checks in healthy subjects. There is a need for better devices for monitoring metabolism.

SUMMARY

Accordingly, one or more aspects of the present disclosure relate to a system for metabolic monitoring comprising: an interface appliance configured to collect exhaled gas from nasal airways of a subject; a mixing chamber operatively connected with the interface appliance, the mixing chamber configured to receive at least a portion of the exhaled gas from the interface appliance; a plurality of sensors configured to output signals related to one or more gas parameters related to inhaled gas and exhaled gas by the subject during one or more breaths; and one or more physical computer processors operatively connected with the sensors to receive the output signals, the one or more physical computer processors configured by computer readable instructions to: determine a flow rate of gas in the interface appliance during the one or more breaths based on the output signals from the sensors; determine pressure changes near the mouth of the subject during the one or more breaths based on the output signals from the sensors to detect mouth breathing of the subject; determine concentration measurements of O2 and CO2 of the portion of the exhaled gas in the mixing chamber based on the output signals from the sensors, and discard concentration measurements corresponding to mouth breathing; determine a rate of oxygen consumption VO2 and a carbon dioxide production VCO2 of the subject based on the determined flow rate of gas, the determined carbon dioxide concentration of the exhaled gas in the mixing chamber, and the determined oxygen concentration of the exhaled gas in the mixing chamber.

Another aspect of the present disclosure provides a method for metabolic monitoring comprising: collecting, with an interface appliance, exhaled gas from nasal airways of a subject; receiving at least a portion of the exhaled gas from the interface appliance in a mixing chamber operatively connected with the interface appliance; receive, from a plurality of sensors, output signals related to one or more gas parameters related to inhaled gas and exhaled gas by the subject during one or more breaths; determine, with one or more physical computer processors, a flow rate of gas in the interface appliance during the one or more breaths based on the output signals from the sensors; determine, with one or more physical computer processors, pressure changes near the mouth of the subject during the one or more breaths based on the output signals from the sensors to detect mouth breathing of the subject; determine, with one or more physical computer processors, concentration measurements of O2 and CO2 of the portion of the exhaled gas in the mixing chamber based on the output signals from the sensors, and discard concentration measurements corresponding to mouth breathing; and determine, with one or more physical computer processors, a rate of oxygen consumption VO2 and a carbon dioxide production VCO2 of the subject based on the determined flow rate of gas, the determined carbon dioxide concentration of the exhaled gas in the mixing chamber, and the determined oxygen concentration of the exhaled gas in the mixing chamber.

Still another aspect of the present disclosure relates to a system for metabolic monitoring comprising: means for collecting exhaled gas from nasal airways of a subject; means for receiving at least a portion of the exhaled gas from the interface appliance; sensing means for outputting signals related to one or more gas parameters related to inhaled gas and exhaled gas by the subject during one or more breaths; means for determining a flow rate of gas in the means for collecting exhaled gas during the one or more breaths based on the output signals from the sensing means; means for determining pressure changes near the mouth of the subject during the one or more breaths based on the output signals from the sensing means to detect mouth breathing of the subject; means for determining concentration measurements of O2 and CO2 of the portion of the exhaled gas in the means for receiving at least a portion of the exhaled gas based on the output signals from the sensing means, and discard concentration measurements corresponding to mouth breathing; and means for determining a rate of oxygen consumption VO2 and a carbon dioxide production VCO2 of the subject based on the determined flow rate of gas, the determined carbon dioxide concentration of the exhaled gas in the means for receiving at least a portion of the exhaled gas, and the determined oxygen concentration of the exhaled gas in the means for receiving at least a portion of the exhaled gas.

These and other objects, features, and characteristics of the present disclosure, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the disclosure.

DETAILED DESCRIPTION OF EXEMPLARY EMBODIMENTS

Figure 1:
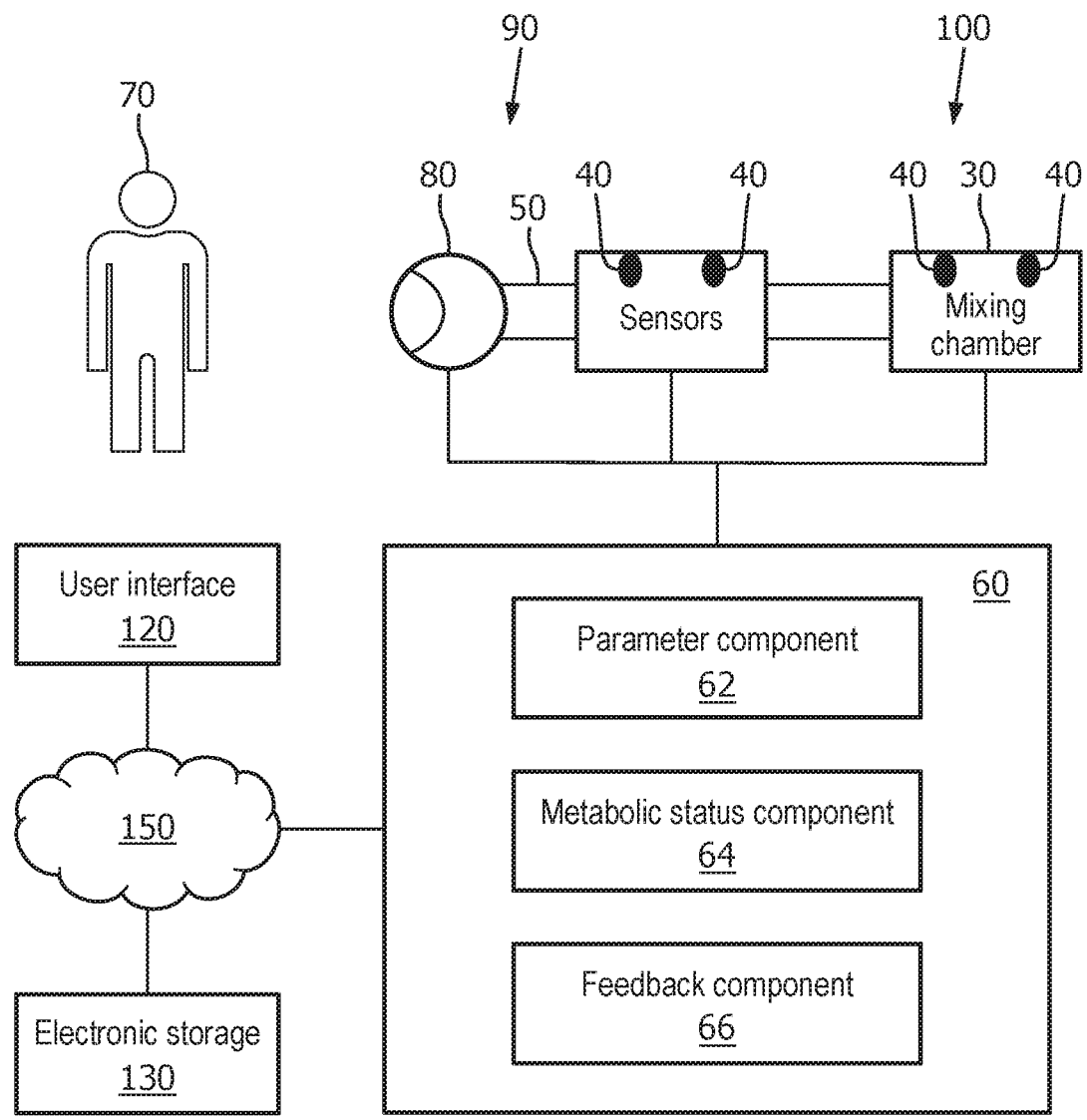
FIG. 1 illustrates a system for nocturnal metabolic monitoring, according to one or more embodiments.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

FIG. 1 illustrates an example of a system 100 for metabolic monitoring, according to one or more embodiments of the present disclosure. In some embodiments, system 100 is configured for metabolic monitoring while the subject is inactive (e.g., asleep). In some embodiments, system 100 is configured for nocturnal metabolic monitoring. System 100 may allow a subject's metabolism to be monitored at home (during the night and without the need of skilled personnel) instead of requiring the use of metabolic rooms or other equipment available only in specialized facilities for costly and sporadic measurements. The continuous monitoring of metabolism and its changes may provide insight into basal energy expenditure as well as available stores of glycogen and may be used to tailor meals and physical activity in order to optimize weight and energy management.

In some embodiments, system 100 may provide information about the metabolic status of the subject based on oxygen consumption ($VO_2$) and carbon dioxide production ($VCO_2$) measurements, and their changes overnight. In some embodiments, system 100 includes a mixing chamber used for gas analysis (e.g., $CO_2$ and $O_2$ concentration measurements). The mixing chamber may be made small and relatively portable. Other than wearing the interface, the subject's collaboration is not required. $VO_2$ and $VCO_2$ measurements may be used to estimate a subject's energy expenditure (EE) and respiratory quotient (RQ). Energy expenditure (EE) may be used to assess the caloric need of the individual and respiratory quotient (RQ) may provide information on the macronutrient primarily used to produce energy (e.g., carbohydrates, fat, protein, etc.)

In some embodiments, system 100 comprises a subject interface 90 designed to collect all exhaled gas (e.g., continuously, at every breath) at the nose of the subject during one or more breaths for further analysis. In some embodiments, system 100 is configured (e.g., with pressure sensor 44) to detect mouth breaths in order to discard invalid measurements (measurements that include mouth breathing). This provides for a more accurate determination of $VO_2$, $VCO_2$, EE, and/or RQ. In turn, system 100 provides a better picture of the subject's nocturnal metabolism status.

In some embodiments, system 100 comprises a subject interface 90, one or more sensors 40, a mixing chamber 30, one or more physical computer processors 60, a user interface 120, electronic storage 130, a network 150, and/or other components.

In some embodiments, subject interface 90 is configured to communicate a flow of breathable gas to the airway of subject 70 (e.g., ambient air). Subject interface 90 is configured to deliver breathable ambient air to the nostrils of the subject and also collect the exhaled gas from the subject's nostrils (e.g., with interface appliance 80). In some embodiments, subject interface 90 comprises a conduit 50, an interface appliance 80, one or more valves 85, and/or other components. In some embodiments, interface appliance 80 is configured to be removably engaging one or more external orifices of the airway of subject 70 (e.g., nostrils) to communicate gas between the airway of subject 70 and subject interface 90. Interface appliance 80 may be removably coupled with conduit 50 (e.g., Interface appliance 80 can be removed for cleaning, replacement, and/or for other purposes.) In some embodiments, interface appliance 80 may include two prongs configured to be placed in the nostrils of the subject and form a seal with the nasal cavities of the subject. Sealing the nasal cavities allows for collecting all the exhaled gas from the subject nostrils for further analysis as described below. Examples of interface appliance 80 may comprise, a nasal cannula, or other non-invasive or invasive interface appliances that communicate the flow of gas with the airway of the subject. The present disclosure is not limited to these examples and contemplates delivery of the flow of gas to the subject using any delivery means.

In some embodiments, subject interface 90 includes valve (s) 85 configured to allow the breathable gas to flow to the subject nostrils. For example, the one or more valves may be located within the interface appliance 80. In some embodiments, valve(s) 85 are configured to allow the breathable gas (e.g., air from the atmosphere) to flow through it in one direction. For example, valve(s) 85 are configured to open during inhalation and close during exhalation. Examples of such valve include one-way valves, check valves, non-return valves, and/or other valves that allow flow of gas in one direction only. In some embodiments, subject interface 90 may be configured to deliver breathable gas to the subject from a gas source (e.g., source of pressurized gas to support the subject breathing).

In some embodiments, sensor(s) 40 are configured to generate output signals conveying information related to one or more breathing parameters of subject 70 during one or more breaths. In some embodiments, the one or more breathing parameters may comprise gas parameters related to the breathable gas provided by the subject interface, breathing parameters related to respiration of subject 70, physiological parameters of subject 70, and/or other parameters. The one or more gas parameters of the breathable gas may comprise, for example, one or more of an inhalation flow rate, an exhalation flow rate, inhaled volume, inhaled volume, pressure, humidity, temperature, acceleration, velocity, gas components concentrations (e.g., $O_2$ concentration, $CO_2$ concentration, etc.), and/or other parameters of the breathable gas. Breathing parameters related to the respiration of subject 70 may comprise a tidal volume, a timing (e.g., beginning and/or end of inhalation, beginning and/or end of exhalation, etc.), an inhalation flow rate, an exhalation flow rate, a respiration rate, a respiration airflow, a duration (e.g., of inhalation, of exhalation, of a breathing cycle, etc.), respiration frequency, effort of breathing, exhaled gas components concentrations (e.g., $O_2$ concentration, $CO_2$ concentration, etc.), and/or other breathing parameters. Physiological parameters may include oximetry parameters, pulse, temperature, blood pressure, and/or other physiological parameters.

In some embodiments, sensor(s) 40 may comprise one or more sensors that measure such parameters directly (e.g., through fluid communication with the subject and/or the subject interface.) In some embodiments, sensor(s) 40 may comprise one or more sensors that generate output signals related to the one or more parameters indirectly (e.g., through measurements from other sensors or other components within or outside system 100). In some embodiments, sensor(s) 40 may include one or more, position sensor for measuring position of subject interface, volume sensor for measuring volume of inhaled and/or exhaled gas, pressure sensor for measuring gas pressure within/or outside subject interface 90, humidity sensor for measuring humidity within and/or outside the subject interface, gas temperature sensor for measuring gas temperature. In some embodiments, sensor(s) 40 may comprise one or more sensors configured to generate output signals related to physiological parameters of subject 70. For example, heart sensor for measuring heart parameters of the subject, motion sensor for detecting subject motion, accelerometer, oximeter, audio sensor, video sensor (camera), and/or other sensors. For example, in some embodiments, sensor(s) 40 include one or more flow sensors 42 (shown in FIGS. 3-4) configured to measure flow rate of the inhaled and/or exhaled gas to or from the subject. Flow sensors 42 may be configured to measure flow rate of gas inhaled by the subject, flow rate of gas exhaled by the subject, flow rate of the exhaled gas within the interface appliance 80, conduit 50, mixing chamber 30, and/or gas flow rate in other locations of system 100.

In some embodiments, sensor(s) 40 include one or more pressure sensors 44 configured to output signals related to gas pressure at one or more locations within system 100. For example, pressure sensors 44 may include a pressure line located at or near the subject mouth and configured to measure pressure at or near the mouth of the subject. In some embodiments, sensor(s) 40 comprise one or more $O_2$ concentration sensors 45 (shown in FIGS. 3-4) configured to output signals related to $O_2$ concentration in the exhaled gas. In some embodiments, the one or more $O_2$ concentration sensors 45 is configured to output signals related to $O_2$ concentration in the inhaled gas. In some embodiments, the one or more $O_2$ concentration sensor 45 is configured to output signals related to $O_2$ concentration in the exhaled gas in the mixing chamber. In some embodiments, sensor(s) 40 include one or more $CO_2$ concentration sensors 47 (shown in FIGS. 3-4) configured to output signals related to $CO_2$ concentration in the exhaled gas. In some embodiments, the one or more $CO_2$ concentration sensors 47 is configured to output signals related to $CO_2$ concentration in the inhaled gas. In some embodiments, CO2 sensors maybe nondispersive infrared (NDIR) CO2 sensors. That said, this is not to be construed as limiting as other CO2 sensors may be considered, which is not to suggest that any other description is limiting.

In some embodiments, the one or more $CO_2$ concentration sensor 45 is configured to output signals related to $CO_2$ concentration in the exhaled gas in the mixing chamber. In some embodiments, the mixing chamber contains the gas sensors as well as sensors of humidity and temperature necessary to correct for those factors in computing gas concentrations from gas sensors. In some embodiments, the exhaled gases sampled via the interface and channeled to the mixing chamber where they are mixed with gases previously sampled and already present in the mixing chamber.

Sensor(s) 40 may comprise sensors disposed in a plurality of locations, such as for example, at various locations within (or in communication with) the interface appliance 80, on subject 70, within (or in communication with) a respiratory device, a conduit 50, and/or other locations. In some embodiments, processor(s) 60 may detect if the state of seal with the nostrils (e.g., based on output signals from sensors 40). For example, processor(s) 60 may be configured to detect leak of exhaled gas (e.g., based on determination of flow rate, and/or pressure at the nostrils, and/or based on or a position of the appliance in relation with the nostrils). In operation, in case of broken seal processor(s) 60 may be configured to discard measurements or send an alert to the subject indicating the seal between the appliance and the nostril is broken.

Figure 2A:
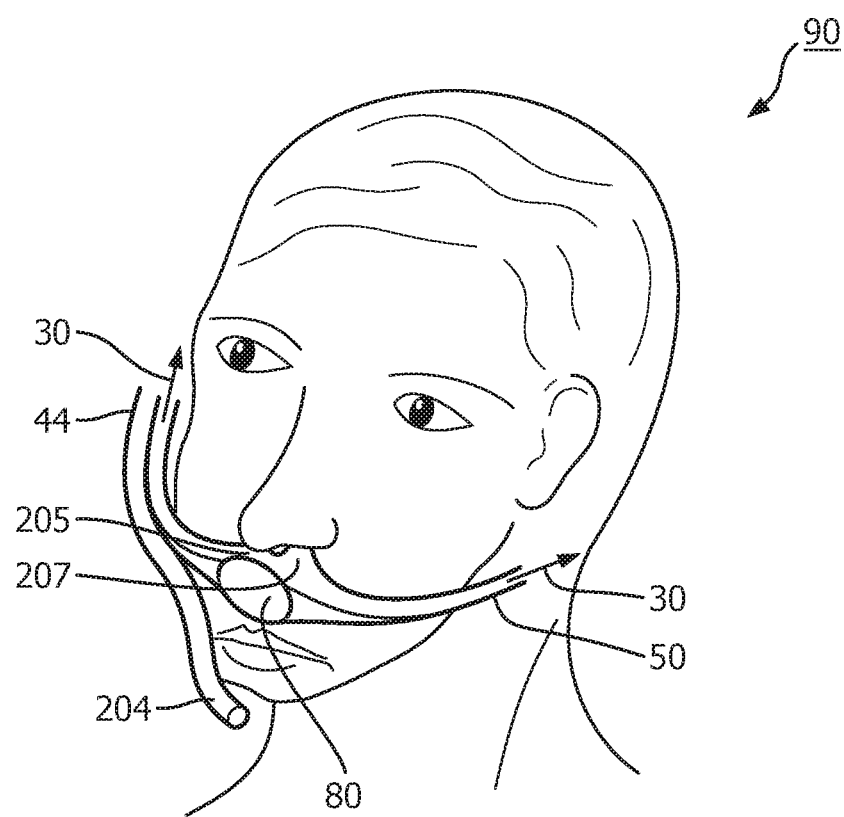
FIG. 2A illustrates an example of an interface appliance, according to one or more embodiments.

FIG. 2A illustrates an example 200 of a subject interface 90, according to one or more embodiments. In these embodiments, subject interface 90 includes interface appliance 80 configured to engage the nostrils of the to communicate gas between the airway of the subject and subject interface 90. Interface appliance 80 includes two prongs 205 and 207 configured to be placed in the nostrils of the subject and form a seal with the nasal cavities of the subject. This will allow collection of all the exhaled gas from the subject nostrils for further measurements and analysis. Subject interface 90 includes conduit 50 operatively connected to interface appliance 80 and configured to direct the exhaled gas to mixing chamber 30 for further measurements and analysis. Subject interface 90 includes pressure sensor 44 configured to measure pressure at or near the mouth of the subject (through pressure line 204 located at or near the mouth) to detect mouth breathing. Mouth breathing can be determined based on changes in the output signals from pressure sensor 44 (indicating pressure changes at or near the subject's mouth.)

In some embodiments, increases in pressure during exhalation (above a predetermined threshold) indicate exhalation through the mouth. Exhalation through the mouth makes the VO2 and VCO2 measurements invalid. Accordingly, processor (60) will discard the VO2 and VCO2 measurements acquired over time windows where mouth exhalations were detected (mouth pressure exceeds threshold). Measurements that include mouth breathing are discarded to provide an accurate determination of the nocturnal metabolism rate of the subject. For example, VO2 and VCO2 measurements that were acquired (as well as the corresponding EE and RQ values that were derived from them) will not be displayed to the user.

As explained below, In some embodiments, processor (60) is configured to discard O2 and CO2 concentration measurement, responsive to detecting pressure changes at or near the mouth (indicating mouth breathing) for every breath. For example, O2 and CO2 concentration measurements are determined for every breath (e.g., for one or more breaths). Responsive to a given breath of the one or more breaths being determined to include mouth breathing, O2 and CO2 concentration for that given breath are discarded (are not used in further analysis and measurements of O2 consumption and/or CO2 production.) In other words, O2 consumption VO2 and/or CO2 production VO2 are only measured for breaths where exhaled gas comes from the nasal airways of the subject. In some embodiments, O2 consumption VO2 and/or CO2 production VCO2 are measured for all breaths (regardless of mouth breathing). In these embodiments, VO2 and VCO2 corresponding to mouth breathing, are subsequently discarded in measurements of energy expenditure EE and respiratory quotient RQ.

Figure 2B:
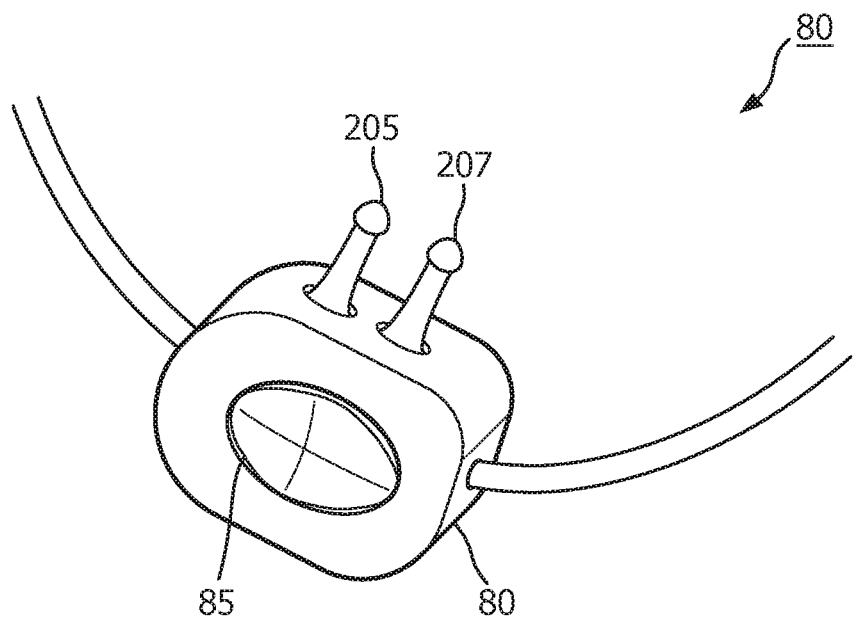
FIGS. 2B-2C illustrate an example of a subject interface, according to one or more embodiments.
Figure 2C:
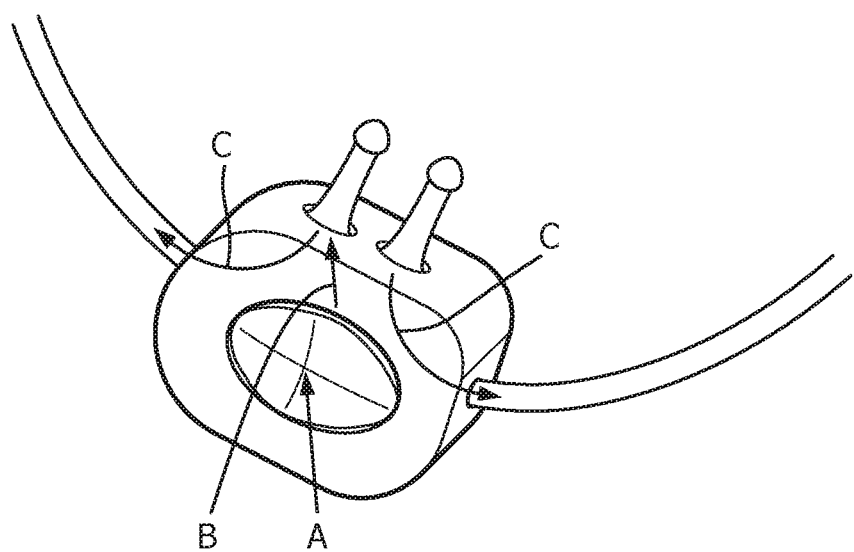

FIG. 2B-2C illustrate an example of an interface appliance 80, according to one or more embodiments. Interface appliance 80 is a nasal interface that includes two prongs 205 and 207 configured to fit in the nostrils of the subject and form a seal with the nasal cavities of the subject. Interface appliance 80 includes a valve 85 configured to direct ambient gas to the airways of the subject (as shown by arrow A in FIG. 2C). Valve 85 may be a passive inhalation valve (e.g., a one-way valve, a check valve, non-return valve, etc.) Active valves may be considered and are compatible with the embodiments of this disclosure. In operation, the inhalation gas (e.g., ambient air) enters the one-way inhalation valve 85 and goes into the nose (through the prongs as shown by arrows B). During exhalation the valve is closed, and the gas is diverted to the tubes (as shown by arrows C in FIG. 2C) leading to the mixing chamber (not shown).

Returning to FIG. 1, system 100 comprises a mixing chamber 30 operatively connected with the subject interface 90. Mixing chamber 30 is configured to collect all or a portion of the exhaled gas. In some embodiments, mixing chamber 30 is configured to include one or more sensor(s) 40 for measuring gas parameter of the exhaled gas within the mixing chamber. For example, O2 concentration, CO2 concentration, flow rate, volume, pressure, etc.

Processor(s) 60 is configured to provide information processing capabilities in system 100. As such, processor(s) 60 may include one or more digital processors, one or more analog processor, one or more digital circuits designed to process information, one or more analog circuits designed to process information, a state machine, and/or other mechanisms for electronically processing information. In some embodiments, processor(s) 60 is operatively connected to sensors (40), mixing chamber 30, subject interface 90, user interface 120, and/or other components of system 100. Although processor(s) 60 is shown in FIG. 1 as a single entity, this is for illustrative purposes only. In some implementations, processor(s) 60 includes a plurality of processing units. These processing units may be physically located within the same device (e.g., sensors(40), mixing chamber 30, subject interface 90, user interface 120, etc.), or processor(s) 60 may represent processing functionality of a plurality of devices operating in coordination and located outside of system 100 (e.g., in the Cloud). In some embodiments, processors (60) may represent processing functionality of a plurality of devices located within and/or outside system 100 (e.g., communicatively coupled via a network 150).

Processor(s) 60 is configured to execute one or more computer program components. The one or more computer program components may comprise one or more of a parameter component 62, a metabolic status component 64, a feedback component 66, and/or other components. Processor(s) 60 may be configured to execute components 62, 64, and 66 by software; hardware; firmware; some combination of software, hardware, and/or firmware; and/or other mechanisms for configuring processing capabilities on Processor(s) 60.

It should be appreciated that although components 62, 64, and 66 are illustrated in FIG. 1 as being co-located within a single processing unit, in implementations in which Processor(s) 60 comprises multiple processing units, one or more of components 62, 64, and 66 may be located remotely from the other components. The description of the functionality provided by the different components 62, 64, and 66 described below is for illustrative purposes, and is not intended to be limiting, as any of components 62, 64, and 66 may provide more or less functionality than is described. For example, one or more of components 62, 64, and 66 may be eliminated, and some or all of its functionality may be provided by other components 62, 64, and/or 66. As another example, Processor(s) 60 may be configured to execute one or more additional components that may perform some or all of the functionality attributed below to one of components 62, 64, and/or 66.

In some embodiments, parameter component 62 is configured to receive, determine and/or obtain one or more parameters (e.g., from components within or outside system 100). the one or more parameters may be determined based on the output signals from sensor(s) 40. In some embodiments, parameter component 62 is configured to determine one or more breathing parameters related to respiration of subject 70, one or more parameters of a breathable gas within system 100, (e.g., parameters related to flow of breathable gas delivered by a respiratory device), one or more physiological parameters of subject 70, and/or other parameters. The breathing parameters related to the respiration of subject 70 may comprise beginning and/or end of individual breaths. In some embodiments, the breathing parameters may comprise a tidal volume, a timing (e.g., beginning and/or end of inhalation, beginning and/or end of exhalation, etc.), a respiration rate, a duration (e.g., of inhalation, of exhalation, of a single breathing cycle, etc.), respiratory airflow, breathing effort, respiration frequency, and/or other breathing parameters. The one or more gas parameters of the flow of breathable gas delivered to the subject may comprise, for example, one or more of a flow rate, heart rate, volume, pressure, humidity, temperature, acceleration, velocity, and/or other gas parameter. Physiological parameters may include oximetry parameters, a pulse, temperature, blood pressure, movement, and/or other physiological parameters.

In some embodiments, parameter component 62 is configured to determine flow rate of the exhaled gas based on the output signals from one or more sensor(s) 40 (e.g., flow sensor 42). In some embodiments, parameter component 62 is configured to determine inhalation flow rate, exhalation flow rate, and/or other gas flow rates within subject interface 90 (or the interface appliance 80). In some embodiments, the entire exhalation flow rate is determined. As explained above, interface appliance 80 is configured to form a seal with the nostrils to allow for collecting the entire exhaled gas. In some embodiments, parameter component 62 is configured to determine flow rate of a portion of the exhaled gas. For example, in some embodiments, the exhaled gas is sampled (after the overall exhaled gas has been collected). For example, in some embodiments, the sample is a constant proportion of the flow is directed to the mixing chamber for further measurements (e.g., $O_2$ and $CO_2$ concentrations measurements). In some embodiments, parameter component 62 is configured to determine volume of air inhaled, and/or volume of air exhaled. For example, based on output signals from volume sensors within subject interface 90, mixing chamber 30, and/or other locations within or outside system 100. In some embodiments, volume of inhaled and/or exhaled gas may be determined based on output signals from flow rate sensors 42.

In some embodiments, parameter component 62 is configured to determine pressure in one or more locations within or outside system 100. In some embodiments, parameter component 62 is configured to determine pressure at or near the mouth of the subject. In some embodiments, pressure may be determined based on the output signals from one or more sensor(s) 40 (e.g., pressure sensor 44). In some embodiments, parameter component 62 is configured to determine pressure changes at or near the mouth of the subject.

In some embodiments, parameter component 62 is configured to measure $O_2$ concentration in the exhaled gas and/or inhaled gas by the subject. In some embodiments, parameter component 62 is configured to measure $O_2$ concentration in a portion of the exhaled gas in the mixing chamber. In some embodiments, $O_2$ concentration is measured based on output signals from $O_2$ sensors 45. As indicated above, the $O_2$ sensors may be located in the mixing chamber, or in other location of the appliance interface. In some embodiments, parameter component 62 is configured to measure $CO_2$ concentration in the exhaled gas from the subject. In some embodiments, parameter component 62 is configured to measure $CO_2$ concentration in a portion of the exhaled gas in the mixing chamber In some embodiments, $CO_2$ concentration is measured based on output signals from $CO_2$ sensors. As indicated above, the $CO_2$ sensors may be located in the mixing chamber, or in other location of the appliance interface. In some embodiments, parameter component 62 is configured to discard O2 and CO2 concentration measurement, responsive to detecting pressure changes at or near the mouth (indicating mouth breathing). For example, in some embodiments, parameter component measure O2 and CO2 concentration for every breath (e.g., for one or more breaths). If a given breath of the breaths is determined to include mouth breathing, O2 and CO2 concentration for that given breath are discarded (are not used in further analysis and measurements of O2 consumption and/or CO2 production.) In other words, O2 consumption and/or CO2 production are only measured for breaths where exhaled gas comes from the nasal airways of the subject. In some embodiments, O2 consumption $VO_2$ and/or CO2 production $VCO_2$ are measured for all breaths (regardless of mouth breathing). In these embodiments, VO2 and VCO2 corresponding to mouth breathing (based on pressure sensor output) are discarded in measurements of energy expenditure EE and respiratory quotient RQ.

In some embodiments, metabolism status component 64 is configured to determine $CO_2$ production ($VCO_2$) in the exhaled gas based on the determined $CO_2$ concentration in the mixing chamber. For example, in some embodiments, $VCO_2$ can be calculated as the rate of carbon dioxide production in milliliters per minute. In some embodiments, metabolism status component 64 is configured to determine $O_2$ consumption $VO_2$ by the subject. In some embodiments, the $O_2$ consumption $VO_2$ is determined based on the determined $O_2$ concentration in the mixing chamber, volume of air inhaled, volume of air exhaled, and concentration of $O_2$ in the inhaled gas.

In some embodiments, metabolism status component 64 is configured to calculate energy expenditure EE and respiratory quotient RQ based on the $VO_2$ and $VCO_2$ measurements. In some embodiments, EE may be used to assess the caloric need of the subject. RQ may be used to provide information on the macronutrient primarily used to produce energy (carbohydrates, fat, protein). In some embodiments, respiratory quotient RQ is the ratio: $VCO_2/VO_2$. In some embodiments, energy expenditure EE (metabolic rate) may be calculated using the following formula:

$$\text{Metabolic rate (kcal per day)} = 1.44(3.94VO_2 + 1.11VCO_2)$$

where $VO_2$ is oxygen consumption in milliliters per minute and $VCO_2$ is the rate of carbon dioxide production in milliliters per minute. The formula can also be written for units of calories per minute:

$$\text{Metabolic rate (Cal per minute)} = 3.94VO_2 + 1.11VCO_2.$$

In some embodiment, Feedback component 66 is configured to display the measured parameters (e.g., $VO_2$, $VCO_2$, EE, RQ, and/or other parameters determined by components 62 and 64). The measurements and recommendations may be displayed via a graphical interface (e.g., user interface 120, dedicated display, laptop, smartphone or similar). In some embodiments, Feedback component 66 is configured to provide recommendations on optimal nutrition and activity behavior to manage weight (e.g., meals and/or activity based on the measurements as well as goals set by the user (e.g., lose weight, optimize physical performance).

Figure 3:
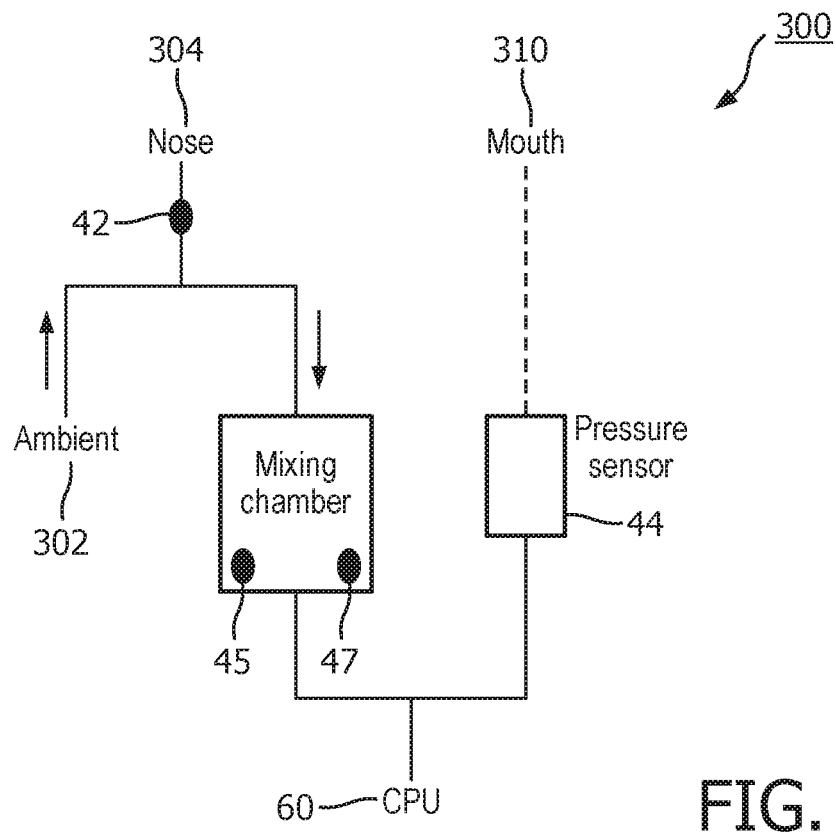
FIG. 3 illustrates an example of a system for nocturnal metabolic monitoring, according to one or more embodiments.

FIG. 3 illustrates an example 300 of a system for nocturnal metabolic monitoring, according to one or more embodiments. In this example, ambient air 302 is directed to the subject nose 304 (e.g., through a subject interface having a valve similar to the subject interface of FIG. 1). Exhaled gas from the subject nose is directed to mixing chamber 30 where $O_2$ and $CO_2$ concentration are measured. Processor(s) 60 determines $VO_2$, $VCO_2$, EE and RQ based on the $O_2$ and $CO_2$ concentration measured in mixing chamber 30. Pressure changes at or near the mouth 310 are measured with pressure sensor 44 to detect mouth breathing. Measurements that include mouth breathing are discarded for a better metabolism rate determination.

Figure 4:
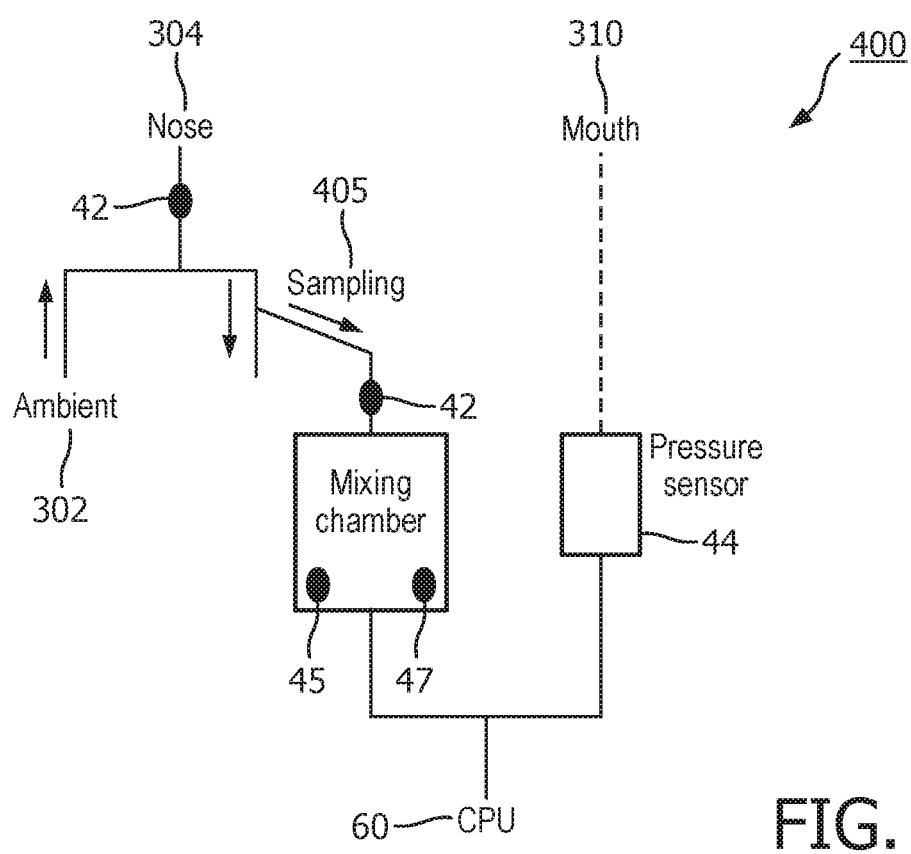
FIG. 4 illustrates an example of a system for nocturnal metabolic monitoring, according to one or more embodiments.

FIG. 4 illustrates an example 400 of a system for nocturnal metabolic monitoring, according to one or more embodiments. In this example, ambient air 302 is directed to the subject nose 304. the collected exhaled gas is sampled (after the overall exhaled gas has been collected) and the sample 405 is directed to the mixing chamber 30 for further measurements. In some embodiments, a constant proportion of the flow is collected in the mixing chamber. In some cases, 2% of the overall exhaled gas is directed to the mixing chamber 30 where $O_2$ and $CO_2$ concentration are measured. Processor(s) 60 determines $VO_2$, VC $O_2$, EE and RQ based on the $O_2$ and $CO_2$ concentration measured in mixing chamber 30. Pressure changes at or near the mouth 310 are measured with pressure sensor 44 to detect mouth breathing. Measurements that include mouth breathing are discarded for a better metabolism rate determination. A difference between the embodiments in FIG. 3 and FIG. 4 is that, in the embodiment on FIG. 3, all exhaled gas goes to the mixing chamber where $O_2$ and $CO_2$ measurements are carried out; in the embodiment on FIG. 4, a proportional sample of the exhaled gas (i.e., a fixed percentage of the overall flow at any moment in time) goes to the mixing chamber, the rest goes directly to the ambient. Both configurations allow for the measurements of $VO_2$ and $VCO_2$, offering different trade-offs between accuracy and size.

User interface 120 is configured to provide an interface between system 100 and subject 70 and/or other users through which subject 70 and/or other users may provide information to and receive information from system 100. Other users may comprise, for example, a caregiver, a doctor, and/or other users. This enables data, cues, results, and/or instructions and any other communicable items, collectively referred to as "information," to be communicated between a user (e.g., subject 70), Processor(s) 60, and/or other components of system 100. As another example, sleep stages, sleep duration, breathing feature distribution, therapy information feedback, the breath rate of subject 70, and/or other information may be displayed to a user (e.g., subject 70) via user interface 120. Examples of interface devices suitable for inclusion in user interface 120 comprise a keypad, buttons, switches, a keyboard, knobs, levers, a display screen, a touch screen, speakers, a microphone, an indicator light, an audible alarm, a printer, a tactile feedback device, and/or other interface devices. In one embodiment, user interface 120 comprises a plurality of separate interfaces.

It is to be understood that other communication techniques, either hard-wired or wireless, are also contemplated by the present disclosure as user interface 120. For example, the present disclosure contemplates that user interface 120 may be integrated with a removable storage interface provided by electronic storage 130. In this example, information may be loaded into system 100 from removable storage (e.g., a smart card, a flash drive, a removable disk, etc.) that enables the user(s) to customize the implementation of system 100. Other exemplary input devices and techniques adapted for use with system 100 as user interface 120 comprise, but are not limited to, an RS-232 port, RF link, an IR link, modem (telephone, cable or other). In short, any technique for communicating information with system 100 is contemplated by the present disclosure as user interface 120.

In some embodiments, electronic storage 130 comprises electronic storage media that electronically stores information. The electronic storage media of electronic storage 130 may comprise one or both of system storage that is provided integrally (i.e., substantially non-removable) with system 100 and/or removable storage that is removably connectable to system 100 via, for example, a port (e.g., a USB port, a firewire port, etc.) or a drive (e.g., a disk drive, etc.). Electronic storage 130 may comprise one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 130 may store software algorithms, information determined by Processor(s) 60, information received via user interface 120, and/or other information that enables system 100 to function properly. Electronic storage 130 may be (in whole or in part) a separate component within system 100, or electronic storage 130 may be provided (in whole or in part) integrally with one or more other components of system 100 (e.g., user interface 120, Processor(s) 60, etc.)

Network 150 may include the Internet and/or other networks, Intranets, a PAN (Personal Area Network), a LAN (Local Area Network), a WAN (Wide Area Network), a SAN (Storage Area Network), a MAN (Metropolitan Area Network), near field communication, frequency (RF) link, Bluetooth, Wi-Fi, Li-FI, a cellular communications network, a Public Switched Telephone Network, and/or any type(s) of wired or wireless network(s). It will be appreciated that this is not intended to be limiting and that the scope of this disclosure includes embodiments in which the components of system 100 are operatively linked via some other communication media. In some cases, the network is a secure local area network, such as a wired Ethernet network behind a firewall.

Information determined by Processor(s) 60 and/or stored by electronic storage 130 may comprise information related to sensor measurements, respiration of subject 70, metabolism rate, feedback, and/or other information. The information stored by electronic storage 130 may be viewed via user interface 120, by connecting (wired and/or wireless) to a separate computer, and/or other via other methods. The information stored by electronic storage 130 may be used, for example, to adjust therapy settings, used by a doctor to make medical decisions, and/or for other uses. In some embodiments, system 100 may include a wireless transmitter (not shown) and the information determined by Processor(s) 30, the information stored by electronic storage 130, and/or other information may be communicated to a caregiver, for example, over a wireless network. By way of a non-limiting example, the caregiver may receive use information, subject status, and/or other information, allowing the caregiver to remotely track the therapy delivered by system 100.

In some embodiments, processing functionality of system 100, described herein, is accomplished locally in a therapy device (e.g., a sensor, a respirator therapy device, etc.) that includes the components of system 100 described above. In some embodiments, processing functionality of system 100 described herein is accomplished outside of system 100 (e.g., remotely by one or more devices connected to system 100 via network 100.) I some embodiments, the processing functionality described herein, may be a combination of processing functionality executed locally and processing functionality executed remotely.

Figure 5:
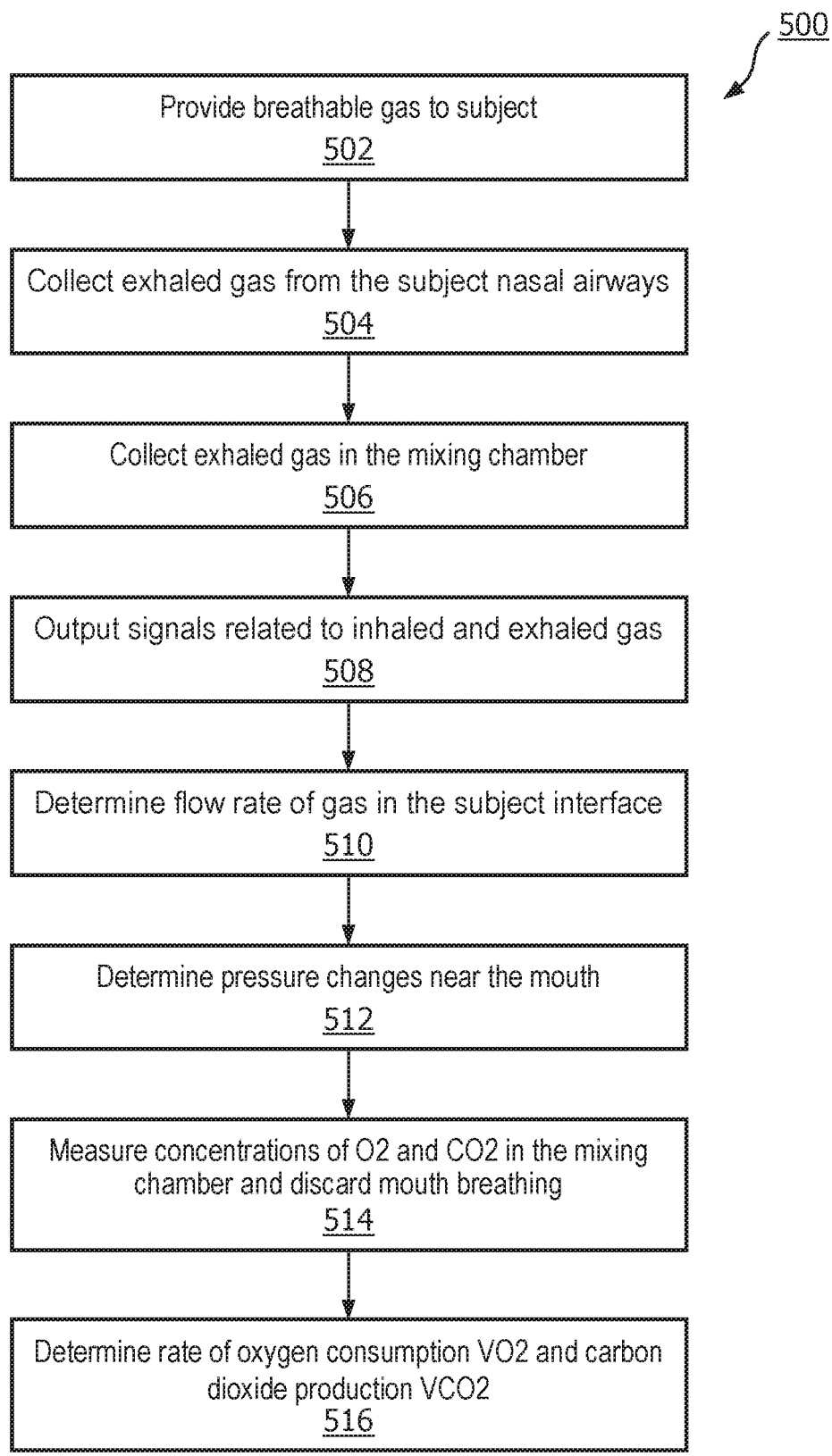
FIG. 5 illustrates a method for nocturnal metabolic monitoring, according to one or more embodiments.

FIG. 5 illustrates a method 500 for u for nocturnal metabolic monitoring. The operations of method 500 presented below are intended to be illustrative. In some embodiments, method 500 may be accomplished with one or more additional operations not described, and/or without one or more of the operations discussed. Additionally, the order in which the operations of method 500 are illustrated in FIG. 5 and described below is not intended to be limiting.

In some embodiments, method 500 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 500 in response to instructions stored electronically on an electronic storage medium. The one or more processing devices may include one or more devices configured through hardware, firmware, and/or software to be specifically designed for execution of one or more of the operations of method 500.

At an operation 502, breathable gas is provided to nasal airways (70) of a subject. In some embodiments, operation 502 is performed by a subject interface the same as or similar to subject interface 90 (shown in FIG. 1 and described herein).

At an operation 504, exhaled gas from the nasal airways is collected. In some embodiments, operation 504 is performed by a subject interface the same as or similar to subject interface 90 (shown in FIG. 1 and described herein).

At operation 506, at least a portion of the exhaled breath gas is collected. In some embodiments, operation 506 is performed by a mixing chamber the same as or similar to mixing chamber 30 (shown in FIG. 1 and described herein).

At an operation 508, output signals related to one or more gas parameters related to inhaled gas and exhaled gas by the subject during one or more breaths are received. In some embodiments, operation 508 is performed by a plurality of sensors the same as or similar to sensor(s) 40 (shown in FIG. 1 and described herein).

At an operation 510, a flow rate of gas in the subject interface during the one or more breaths is determined based on the output signals. In some embodiments, operation 510 is performed by a physical computer processor the same as or similar to Processor(s) 60 (shown in FIG. 1 and described herein).

At an operation 512, pressure changes near the mouth of the subject during the one or more breaths is determined based on the output signals from the sensors to detect mouth breathing of the subject. In some embodiments, operation 512 is performed by a physical computer processor the same as or similar to Processor(s) 60 (shown in FIG. 1 and described herein).

At an operation 514, concentration measurements of O2 and CO2 of the portion of the exhaled gas in the mixing chamber is determined based on the output signals from the sensors. concentration measurements corresponding to mouth breathing are discarded. In some embodiments, operation 514 is performed by a physical computer processor the same as or similar to Processor(s) 60 (shown in FIG. 1 and described herein).

At an operation 516, a rate of oxygen consumption VO2 and a carbon dioxide production VCO2 of the subject are determined. In some embodiments, rate of oxygen consumption VO2 and a carbon dioxide production VCO2 of the subject are determined based on the measured flow rate of gas, the determined carbon dioxide concentration of the exhaled gas in the mixing chamber, and the determined oxygen concentration of the exhaled gas in the mixing chamber are determined. In some embodiments, operation 516 is performed by a physical computer processor the same as or similar to Processor(s) 60 (shown in FIG. 1 and described herein).

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the description provided above provides detail for the purpose of illustration based on what is currently considered to be the most practical and preferred embodiments, it is to be understood that such detail is solely for that purpose and that the disclosure is not limited to the expressly disclosed embodiments, but, on the contrary, is intended to cover modifications and equivalent arrangements that are within the spirit and scope of the appended claims. For example, it is to be understood that the present disclosure contemplates that, to the extent possible, one or more features of any embodiment can be combined with one or more features of any other embodiment.

What is claimed is:

1. A system for metabolic monitoring comprising:
an interface appliance configured to collect exhaled gas from nasal airways of a subject;
a mixing chamber operatively connected with the interface appliance, the mixing chamber configured to receive at least a portion of the exhaled gas from the interface appliance;
a plurality of sensors configured to output signals related to one or more gas parameters related to inhaled gas and exhaled gas by the subject during one or more breaths; and
one or more physical computer processors operatively connected with the sensors to receive the output signals, the one or more physical computer processors configured by computer readable instructions to:
determine a flow rate of gas in the interface appliance during the one or more breaths based on the output signals from the sensors;
determine pressure changes near a mouth of the subject during the one or more breaths based on the output signals from the sensors to detect mouth breathing of the subject;
determine concentration measurements of oxygen ($O_2$) and carbon dioxide ($CO_2$ of the portion of the exhaled gas in the mixing chamber based on the output signals from the sensors, and discard concentration measurements corresponding to mouth breathing; and
determine a rate of oxygen consumption ($VO_2$) and carbon dioxide production ($VCO_2$) of the subject based on the determined flow rate of gas, the determined carbon dioxide concentration of the exhaled gas in the mixing chamber, and the determined oxygen concentration of the exhaled gas in the mixing chamber.

2. The system of claim 1, wherein the one or more physical computer processors are configured to determine a metabolic status of the subject based on the determined $VO_2$ and $VCO_2$.

3. The system of claim 1, wherein the one or more physical computer processors are configured to measure energy expenditure (EE) and/or respiratory quotient (RQ) based on the determined $VO_2$ and $VCO_2$.

4. The system of claim 1, wherein the interface appliance is configured to seal a nasal cavity of the subject from atmosphere.

5. The system of claim 1, wherein the system is configured to monitor metabolism of the subject while the subject is inactive.

6. The system of claim 1, wherein the sensors include a pressure sensor configured to be located near the mouth of the subject, the pressure sensor configured to output pressure signals related to pressure near the mouth of the subject; and wherein the concentration measurements of $O_2$ and $CO_2$ are discarded based upon the output pressure signals from the pressure sensor.

7. The system of claim 1, wherein the interface appliance is configured to provide breathable gas to the nasal airways of the subject.

8. A method for metabolic monitoring comprising:
collecting, with an interface appliance, exhaled gas from nasal airways of a subject;
receiving at least a portion of the exhaled gas from the interface appliance in a mixing chamber operatively connected with the interface appliance;

receiving, from a plurality of sensors, output signals related to one or more gas parameters related to inhaled gas and exhaled gas by the subject during one or more breaths;

determining, with one or more physical computer processors, a flow rate of gas in the interface appliance during the one or more breaths based on the output signals from the sensors;

determining, with the one or more physical computer processors, pressure changes near a mouth of the subject during the one or more breaths based on the output signals from the sensors to detect mouth breathing of the subject;

determining, with the one or more physical computer processors, concentration measurements of oxygen ($O_2$) and carbon dioxide ($CO_2$) of the portion of the exhaled gas in the mixing chamber based on the output signals from the sensors, and discarding concentration measurements corresponding to mouth breathing; and determining, with the one or more physical computer processors, a rate of oxygen consumption ($VO_2$) and carbon dioxide production ($VCO_2$) of the subject based on the determined flow rate of gas, the determined carbon dioxide concentration of the exhaled gas in the mixing chamber, and the determined oxygen concentration of the exhaled gas in the mixing chamber.

9. The method of claim 8, further comprising determining a metabolic status of the subject based on the determined $VO_2$ and $VCO_2$.

10. The method of claim 8, further comprising measuring energy expenditure (EE) and/or respiratory quotient (RQ) based on the determined $VO_2$ and $VCO_2$.

11. The method of claim 8, further comprising sealing, with the interface appliance, a nasal cavity of the subject from atmosphere.

12. The method of claim 8, further comprising monitoring metabolism of the subject while the subject is inactive.

13. The method of claim 8, further comprising receiving, from a pressure sensor located near the mouth of the subject, output pressure signals related to pressure near the mouth of the subject; wherein the plurality of sensors comprises the pressure sensor, and wherein the concentration measurements of $O_2$ and $CO_2$ are discarded based upon the output pressure signals from the pressure sensor.

14. The method of claim 8, further comprising providing, with the interface appliance, breathable gas to the nasal airways of the subject.

15. A system for metabolic monitoring comprising:
means for collecting exhaled gas from nasal airways of a subject;
means for receiving at least a portion of the exhaled gas from the means for collecting exhaled gas;
sensing means for outputting signals related to one or more gas parameters related to inhaled gas and exhaled gas by the subject during one or more breaths;
means for determining a flow rate of gas in the means for collecting exhaled gas during the one or more breaths based on the output signals from the sensing means;
means for determining pressure changes near a mouth of the subject during the one or more breaths based on the output signals from the sensing means to detect mouth breathing of the subject;
means for determining concentration measurements of oxygen ($O_2$) and carbon dioxide ($CO_2$) of the portion of the exhaled gas in the means for receiving at least a portion of the exhaled gas based on the output signals, and for discarding concentration measurements corresponding to mouth breathing; and
means for determining a rate of oxygen consumption ($VO_2$) and carbon dioxide production ($VCO_2$) of the subject based on the determined flow rate of gas, the determined carbon dioxide concentration of the exhaled gas in the means for receiving at least a portion of the exhaled gas, and the determined oxygen concentration of the exhaled gas in the means for receiving at least a portion of the exhaled gas.

16. The system of claim 15, further comprising means for determining a metabolic status of the subject based on the determined $VO_2$ and $VCO_2$.

17. The system of claim 15, further comprising means for measuring energy expenditure (EE) and/or respiratory quotient (RQ) based on the determined $VO_2$ and $VCO_2$.

18. The system of claim 15, wherein the means for collecting the exhaled gas from the nasal airways is configured to seal a nasal cavity of the subject from atmosphere.

19. The system of claim 15, wherein the system is configured to monitor metabolism of the subject while the subject is inactive.

20. The system of claim 15, wherein the sensing means for outputting signals related to one or more gas parameters related to inhaled gas and exhaled gas include a pressure sensing means configured to be located near the mouth of the subject, the pressure sensing means configured to output pressure signals related to pressure near the mouth of the subject; and wherein the concentration measurements of $O_2$ and $CO_2$ are discarded based upon the output pressure signals from the pressure sensing means.

21. The system of claim 15, wherein the means for collecting the exhaled gas from the nasal airways of the subject is further configured to provide breathable gas to the nasal airways of the subject.

* * * * *